(12) United States Patent
Lemaire et al.

(10) Patent No.: US 10,835,675 B2
(45) Date of Patent: Nov. 17, 2020

(54) METHOD AND DEVICE FOR INSERTING NEEDLES

(71) Applicant: DEBIOTECH S.A., Lausanne (CH)

(72) Inventors: Pierre Lemaire, Lausanne (CH); Jérôme Da Ros, Thonon les Bains (FR)

(73) Assignee: DEBIOTECH S.A., Lausanne (CH)

( * ) Notice: Subject to any disclaimer, the term of this patent is extended or adjusted under 35 U.S.C. 154(b) by 96 days.

(21) Appl. No.: 15/225,810

(22) Filed: Aug. 1, 2016

(65) Prior Publication Data

US 2016/0339179 A1 Nov. 24, 2016

Related U.S. Application Data

(62) Division of application No. 13/991,280, filed as application No. PCT/IB2011/055256 on Nov. 23, 2011, now Pat. No. 9,402,984.

(30) Foreign Application Priority Data

Dec. 2, 2010 (EP) ..................................... 10193557

(51) Int. Cl.
*A61M 5/20* (2006.01)
*A61M 37/00* (2006.01)
*A61M 5/158* (2006.01)
*A61M 5/46* (2006.01)

(52) U.S. Cl.
CPC .......... *A61M 5/2033* (2013.01); *A61M 5/158* (2013.01); *A61M 5/46* (2013.01); *A61M 37/0015* (2013.01); *A61M 2005/1585* (2013.01); *A61M 2005/206* (2013.01); *A61M 2005/2026* (2013.01); *A61M 2037/0023* (2013.01); *A61M 2037/0061* (2013.01)

(58) Field of Classification Search
CPC .. A61M 2005/1585; A61M 2005/2026; A61M 2005/206; A61M 2037/0023; A61M 2037/0061; A61M 37/0015; A61M 5/158; A61M 5/2033; A61M 5/46
See application file for complete search history.

(56) References Cited

U.S. PATENT DOCUMENTS

| | | | | |
|---|---|---|---|---|
| 5,271,744 | A * | 12/1993 | Kramer | A61M 5/1723 604/135 |
| 6,102,896 | A * | 8/2000 | Roser | A61M 5/28 604/124 |
| 6,110,147 | A * | 8/2000 | Perouse | A61M 5/3257 604/110 |

(Continued)

*Primary Examiner* — Quynh-Nhu H. Vu
(74) *Attorney, Agent, or Firm* — Nixon & Vanderhye P.C.

(57) ABSTRACT

The invention relates to a device for inserting needles, including a body defined by a proximal end and a distal end, a mounting movably mounted inside the body, at least one needle secured to the mounting, a drive means suitable for driving the mounting towards said distal end, said mounting comprising a distal surface onto which the needle projects, said distal end comprising a contact area intended for contacting the tissue, the mounting being configured so as to reach a position, after activating the driving means, in which the distal surface thereof, relative to said proximal end, is more distant than said contact area, wherein the device is further configured so as to enable a gradual passive return movement of the mounting once said position has been reached.

8 Claims, 11 Drawing Sheets

(56) References Cited

U.S. PATENT DOCUMENTS

Figure 1:
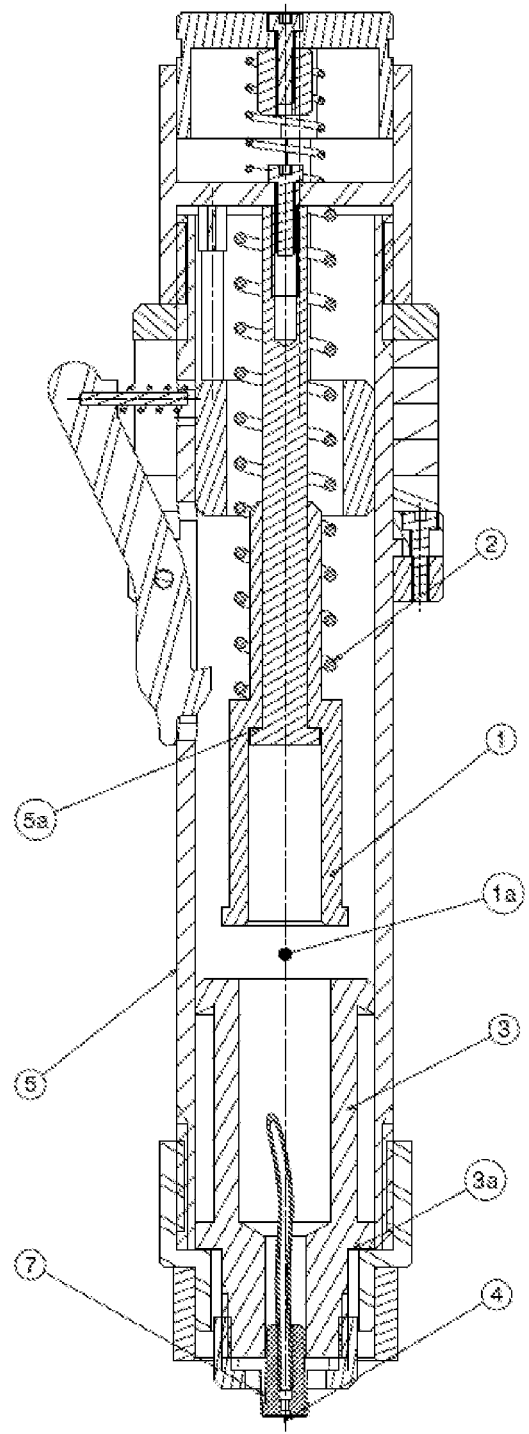

| | | | | |
|---|---|---|---|---|
| 6,210,420 B1 * | 4/2001 | Mauze | ............... | A61B 5/15186 |
| | | | | 606/181 |
| 2004/0092875 A1 * | 5/2004 | Kochamba | ........ | A61M 5/14248 |
| | | | | 604/146 |
| 2004/0116865 A1 * | 6/2004 | Bengtsson | ........ | A61M 5/14248 |
| | | | | 604/171 |
| 2004/0267160 A9 * | 12/2004 | Perez | ............... | A61B 5/150083 |
| | | | | 600/583 |
| 2005/0033230 A1 * | 2/2005 | Alchas | .................. | A61M 5/326 |
| | | | | 604/117 |

* cited by examiner

METHOD AND DEVICE FOR INSERTING NEEDLES

This application is a division of U.S. patent application Ser. No. 13/991,280, filed 3 Jun. 2013, which is the U.S. national phase of International Application No. PCT/162011/055256, filed 23 Nov. 2011, which designated the U.S. and claims priority to EP Application No. 10193557.5, filed 2 Dec. 2010, the entire contents of each of which are hereby incorporated by reference.

FIELD OF THE INVENTION

The present invention relates to the insertion of needles, particularly microneedles. This may be used for intradermal or subcutaneous injection of solutions.

PRIOR ART

Devices for the insertion of microneedles are disclosed in the following documents: U.S. Pat. Nos. 6,743,211, 4,886,499, 7,083,592 and US 20100030148.

GENERAL DESCRIPTION OF THE INVENTION

The present invention constitutes an improvement over the methods and devices of the prior art. It is characterized in particular in that the tissue can be struck by one or more microneedles at relatively high speeds, typically of the order of 7 m/s, while at the same time allowing the tissue to deaden the impact over a certain distance, this having the effect of improving the perforation of the tissue and of returning this tissue to a stable state of equilibrium, thereby minimizing stresses.

In the context of the present invention, the microneedles are free of any physical pressing at the time of injection. The pressure generated by these needles cannot therefore oppose the formation of papules which are brought about by the intradermal injection. It is also possible to follow the growth of the profile of the papule so as to ensure continuity of injection without leaks.

Expressed in a different way, the present invention is characterized by a partial or complete disappearance of the pressure exerted by the needles—or more generally by the needle carrier—on the tissue once the needles have penetrated this tissue, the consequence of this being that the tissue is made to return as closely as possible to its state of equilibrium without residual stress.

A subject of the present invention is, therefore, a device for inserting needles comprising a body defined by a proximal end and a distal end, a carrier mounted with the ability to move inside the body, at least one needle secured to the carrier, drive means designed to drive the carrier toward said distal end and an activation mechanism for activating the drive means, said carrier comprising a distal face from which the needle projects, said distal end comprising a contact zone intended to come into contact with the tissue, the carrier being configured so that it reaches a position, following activation of the drive means, in which its distal face, with respect to said proximal end, is further away than said contact zone; the device being further configured to allow the carrier to recoil in a passive manner once said position has been reached.

In one possible embodiment, the device may have a body of elongate shape in which a piston is slidably mounted, the needle projecting from said piston.

In one possible embodiment, the drive means may be a thruster housing a spring and driving the piston by contact.

In one possible embodiment, the needles of the device are microneedles. Microneedles means needles the dimensions of which are designed to target the intradermal territory. This zone has a thickness that can vary according to the patient and according to the position on the body of one and the same patient. It is of the order of a few hundred microns. However, the microneedle may be slightly longer than the maximum thickness of this zone in order to take account of the fact that the penetration of microneedles into the tissue could be only partial.

In the context of the present invention, the pressure from the start to the end of papule formation is minimal. Once insertion has been achieved, the needle, by way of force exerted on the tissue and on the papule, exerts at most its own weight, that of the carrier and any friction forces that might exist. The physical pressing for fixing the tissue and holding the device in place occurs far from the injection site and any pressing on the device is not transmitted directly to the needle because the piston can slide.

For preference, the device according to the invention is dimensioned in such a way that when applied to the tissue, the needle or needles come into contact with the tissue before the piston becomes restrained by a stop. The length over which the piston is thus deadened by the tissue can range between a fraction of the length of the needle and 10 mm.

If the thruster is restrained by a stop before the needle or needles come into contact with the tissue then the needle or needles, if appropriate connected to an injection line used to deliver a substance, may become detached from the thruster and continue their journey independently of this thruster and thus penetrate the tissue.

Injection may be triggered automatically or manually once the needle or needles are inserted in the tissue, but it will preferably begin once the tissue has returned to its state of equilibrium. Intradermal injection may, in some instances, lead to the formation of a papule which corresponds to the deformation of the tissue following the storage of the solution injected into the tissue, notably during an injection of the bolus type.

It should be noted that the creation and maintaining of a papule are desirable in order to ensure optimal injection. This is why the present invention allows such a papule to form and to remain in place for long enough for the injected substance to diffuse correctly.

A mechanism may make it possible to maintain a maintaining force up to the moment of injection, at which point this force will be canceled.

It should also be noted that, with the present invention, the pressing of the device on the tissue is independent of the pressing of the needle or the needles on the tissue.

It should also be noted that the pressing system of the device also has the task of setting the distance separating the needle or needles from the surface of the tissue before said device is activated.

The invention also relates to a method of insertion and of injection using one or more needles, notably microneedles, and notably into the dermis, in which the needle to which a translational movement has been imparted can decelerate in the tissue because of the elasticity of the tissue over a certain length, while at the same time in fine allowing partial or total spring back to the state of equilibrium (or close to that state) under the simple effect of the elasticity of the tissue. The needle can therefore move freely over a certain distance, which comprises the surface of the tissue. The needle can move into the tissue and push the latter beyond its initial height at equilibrium. Similarly, once the needle is partially inserted in the tissue, a hard, partial or progressive limitation may prevent it from returning backward (opposing force) beyond or not as far as the natural (initial) equilibrium height. The needle will position itself at the point of equilibrium between the elastic force of the tissue and this potential opposing force. For preference, post-insertion equilibrium needs to be as close as possible to the natural equilibrium of the tissue, or even with a slight opposing force to prevent the withdrawal of the needle from the tissue. For preference, the opposing force needs to prevent the needle from coming back out of the tissue through an inertia effect when the tissue regains its equilibrium, but this opposing force needs not to prevent injection. In particular, this opposing force needs not to create any pressure within the tissue that might prevent or limit correct diffusion of the substance that is to be infused.

At the time of the injection, the needle remains secured to the papule, moving with it as it grows, offering a minimum of resistance. A slight opposing force, in addition to the weight if the position is a vertical one, may be present, in order to keep the assembly in place.

For preference, the thruster is set in motion by the release of potential energy, in this instance a spring. This energy may adopt varying forms, plastic spring, leaf spring, gas cartridge, compressed air, electro-magnetic force, generation of gas through chemical reaction between at least two compounds. The piston may be set in motion directly without the aid of a thruster, using only the source of energy. The energy source may be the user himself. By pressing with sufficient force, he will, via a mechanism internal to the device, generate the speed needed to cause the needle or needles to penetrate the tissue.

The device also comprises a safety mechanism, allowing the activation means to be locked in order to avoid unintentional triggering. In the instance discussed here, this is a second safety button that has to be activated before pressing on the insertion trigger. The safety mechanism may adopt various forms, and the pressing of the ring or of the device against the tissue may also unlock the activation trigger.

For preference, the device also comprises a container used to store substance for administering. This container may be positioned on the body of the device, or incorporated directly into the device. Activation of this container, which will cause the substance to be injected into the tissue, may be either manual or automatic. In the latter instance, activation of the device will, once the needles are in place, lead to activation of the container. This container may adopt various forms such as—and this list is not exhaustive—a semirigid reservoir, a flexible pouch, a syringe, a carpule.

The device may comprise a mechanism which makes the needle difficult to access in order to prevent injuries, before or after insertion and after injection when the device has been used for this purpose. This protection may notably be obtained by retracting the needle into the body of the device, or into the carrier itself, or by sliding a cover which prevents access to the needle.

Use of the device is not restricted to a vertical position.

For preference, the device is oriented to allow the needles to penetrate the tissue perpendicularly, although in certain embodiments, this angle may be modified.

DETAILED DESCRIPTION OF THE INVENTION

The invention will be described in greater detail hereinbelow through some nonlimiting embodiments illustrated by figures.

FIG. 1: Depiction of one embodiment of a device according to the invention. A needle (4) is secured to a piston (3) via a connector (7). The thruster (1) is released behind the piston (3), and the empty space (1a) for sliding can be seen between the two of them.

Figure 2:
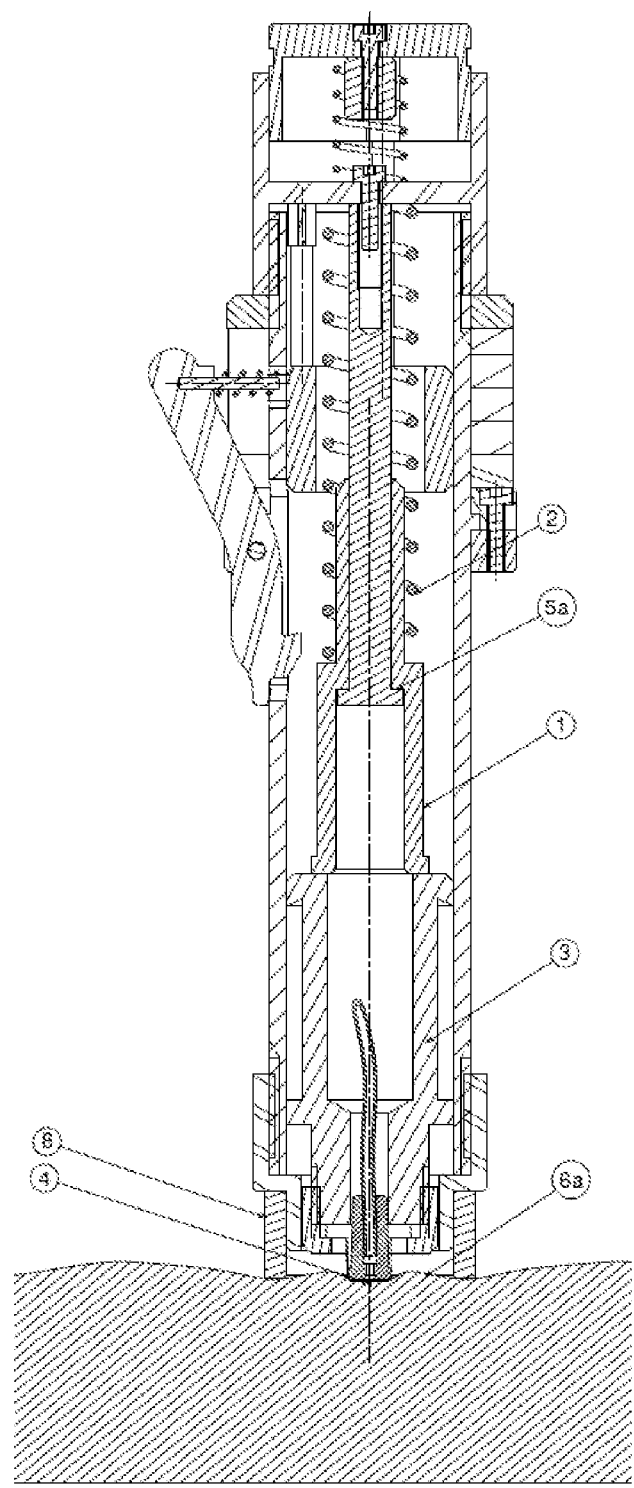

FIG. 2: In this preferred configuration, the device is placed on the tissue (6a) via contact with an outer ring (8). The device has been armed and triggered. The thruster (1) has pushed the piston (3) and has just come into abutment (5a) against a stop (cf. stem in the thruster). The piston (3) will continue its travel under the effect of inertia. For this configuration, the instant at which the piston (3) will detach from the thruster (1) corresponds on average to the instant at which the needle (4) begins to penetrate the tissue.

Figure 3:
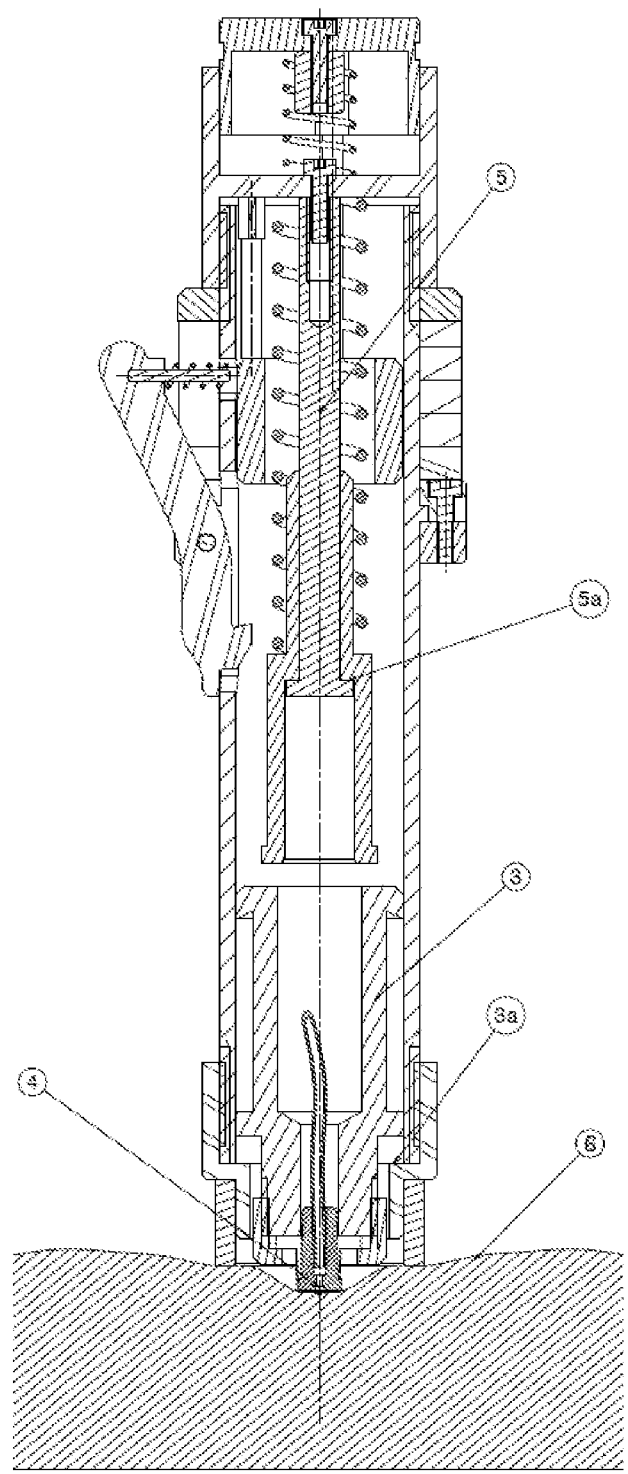

FIG. 3: Same device as that of FIG. 2. The piston (3) has continued its travel under the effect of inertia, the needle (4) penetrates and compresses the tissue (6) to an increasing extent as the elastic return force of the tissue (6) increases with deformation, the piston (3) decelerates until the inertia force drops below the elastic return force, at which point the needle (4) insertion is at a maximum. The movement then reverses with the tissue returning to its "natural" initial state of equilibrium (cf. 6a in FIG. 2).

Figure 4:
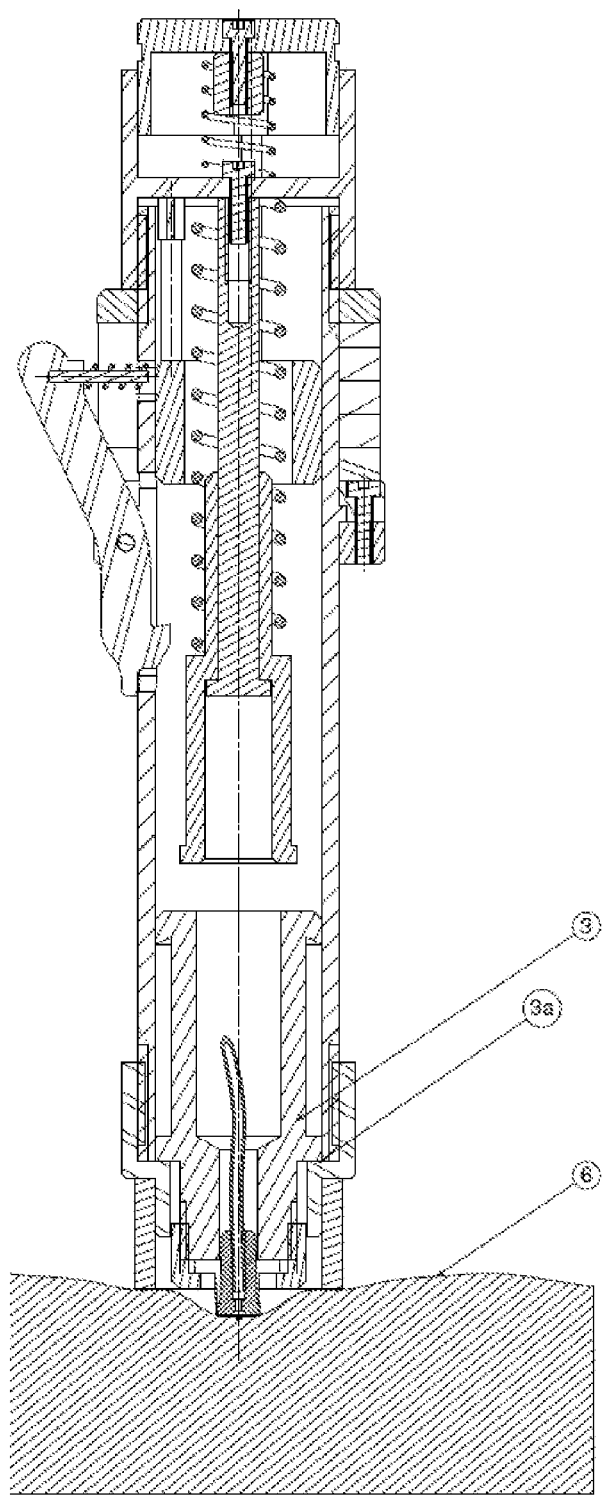

FIG. 4: According to another embodiment, the sizing is such that the piston (3) encounters an abrupt stop (3a) on the body of the device before the inertia force is equalized with the elastic return force of the tissue (6). It is also possible to conceive of partial stop or progressive type of return force.

Figure 5:
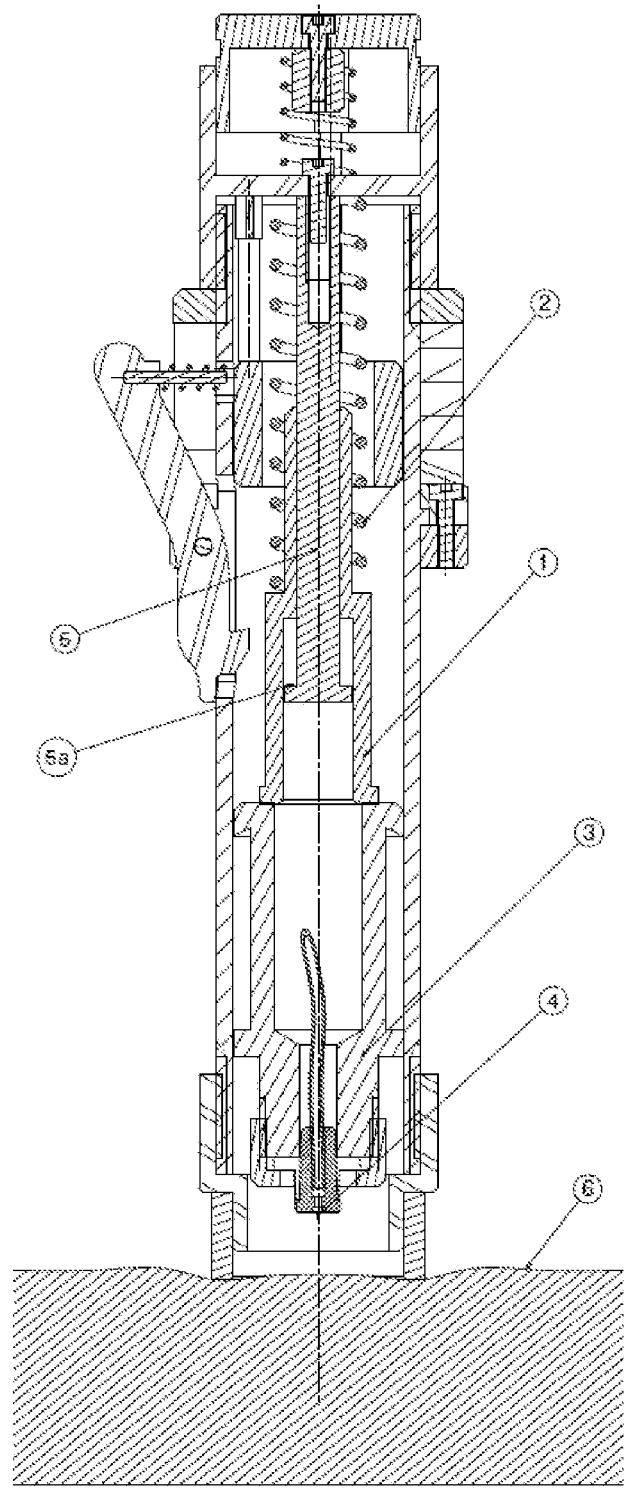
Figure 6:
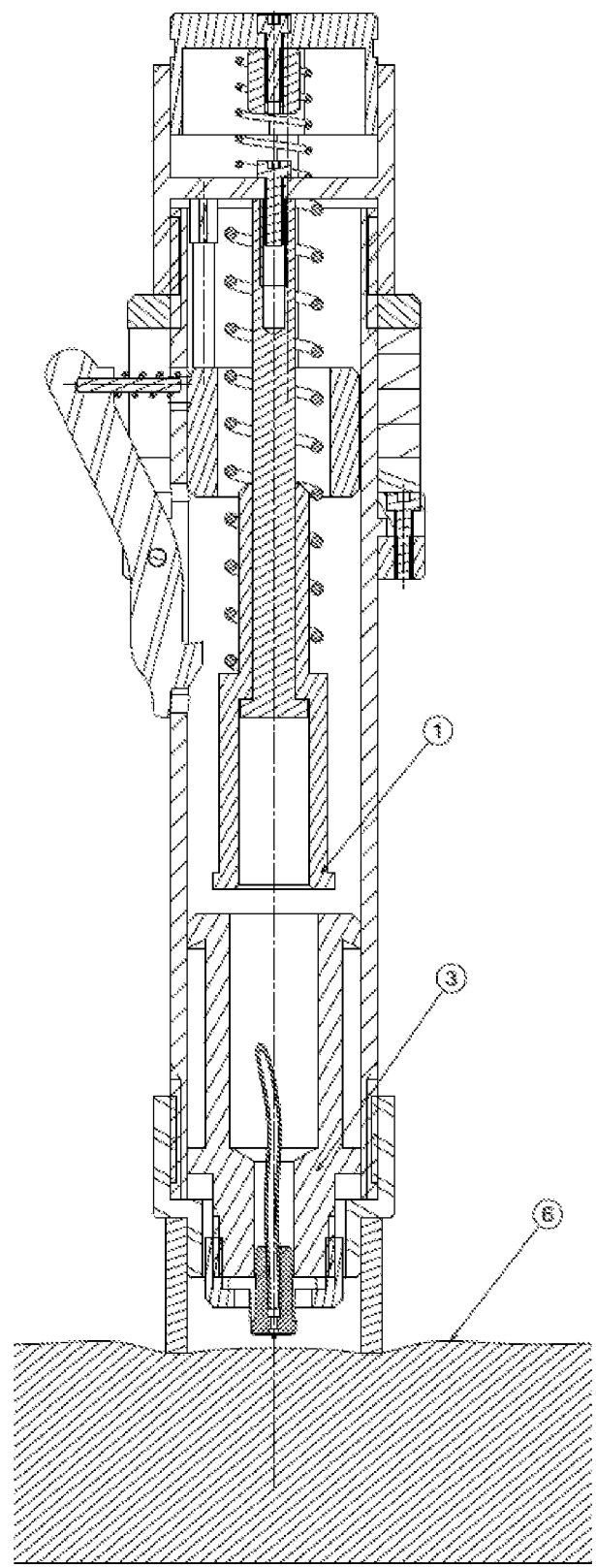

FIGS. 5 and 6: In another variant of the invention, the sizing is such that the piston (3) becomes detached from the thruster when the needle has not yet come into contact with the tissue.

Figure 7:
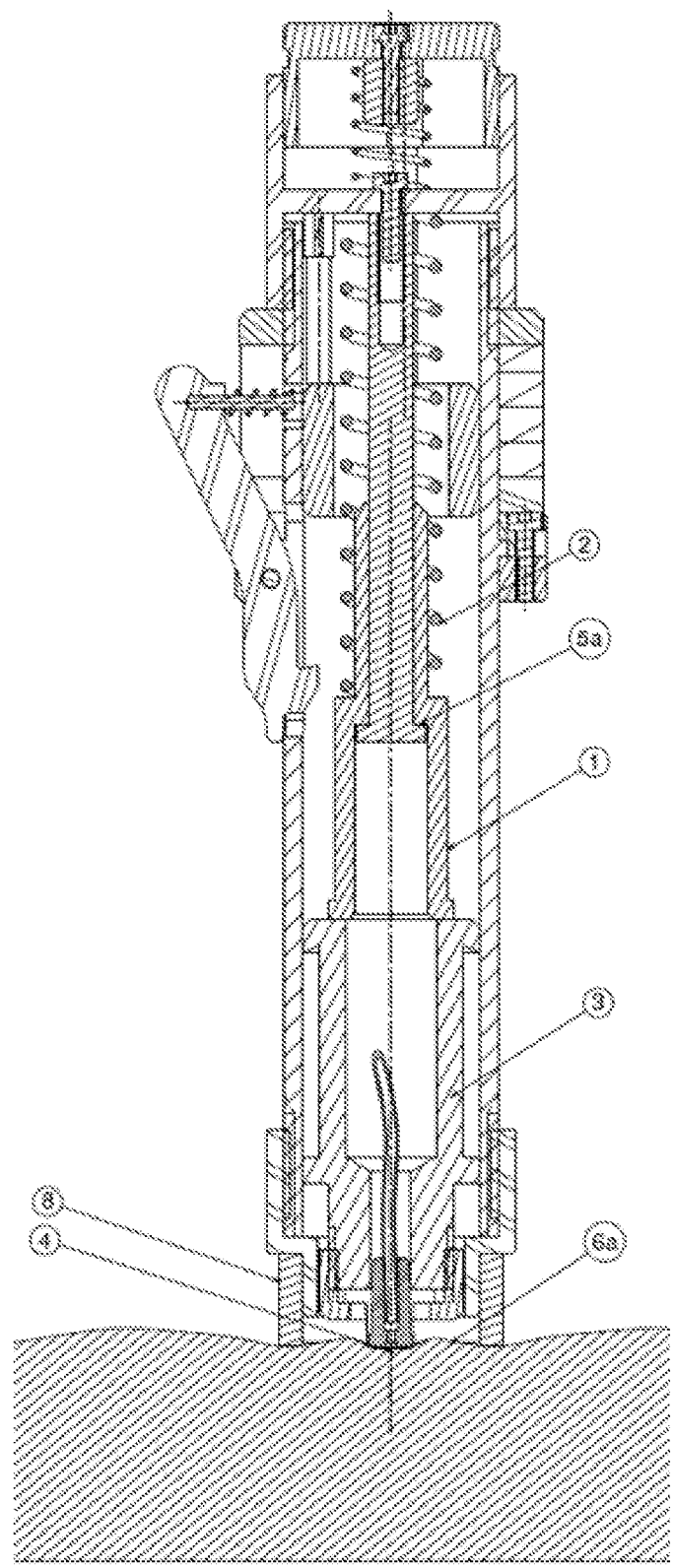

FIG. 7: The elastic force returns the piston (3) to its initial position, the needles (4) remaining well inserted into the tissue (6a); the thruster (1) then offers a return force attenuating any oscillatory effect and preventing the piston (3) from rebounding under the effect of inertia and causing the needle (4) to come out of the tissue (6). Equilibrium is reached with the deformations imposed on the tissue (6) relaxed but with the needle still correctly inserted. A small residual force from the tissue and a small opposing force from the thruster (1) may be enough to keep the needle (4) in place.

Figure 8:
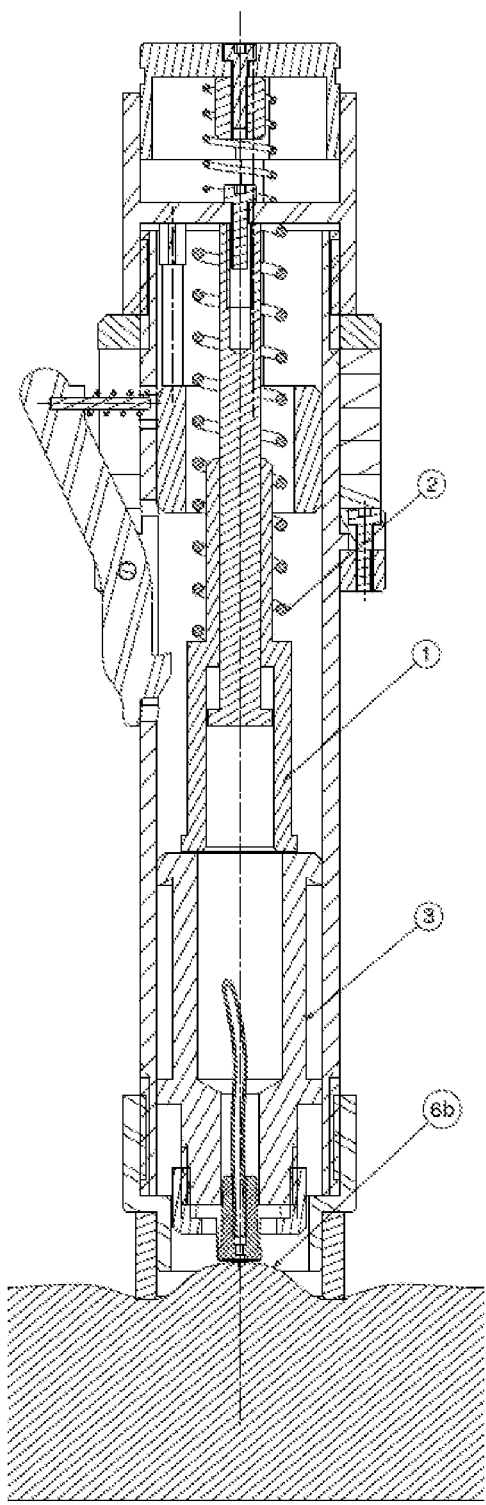

FIG. 8: The injection can begin, preferably at equilibrium, the papule (6b) which is forming drives the piston (3) which can slide without putting up a great deal of resistance and allowing the needle (4) to remain correctly inserted in the papule (6b), guiding the movement. In this instance, the spring (2) of the thruster is at the end of compression and puts up only a weak opposing force opposing the formation of the papule (6b), in addition to the light weight of the assembly comprising piston (3), connector (7), needle (4) and tube.

Figure 9:
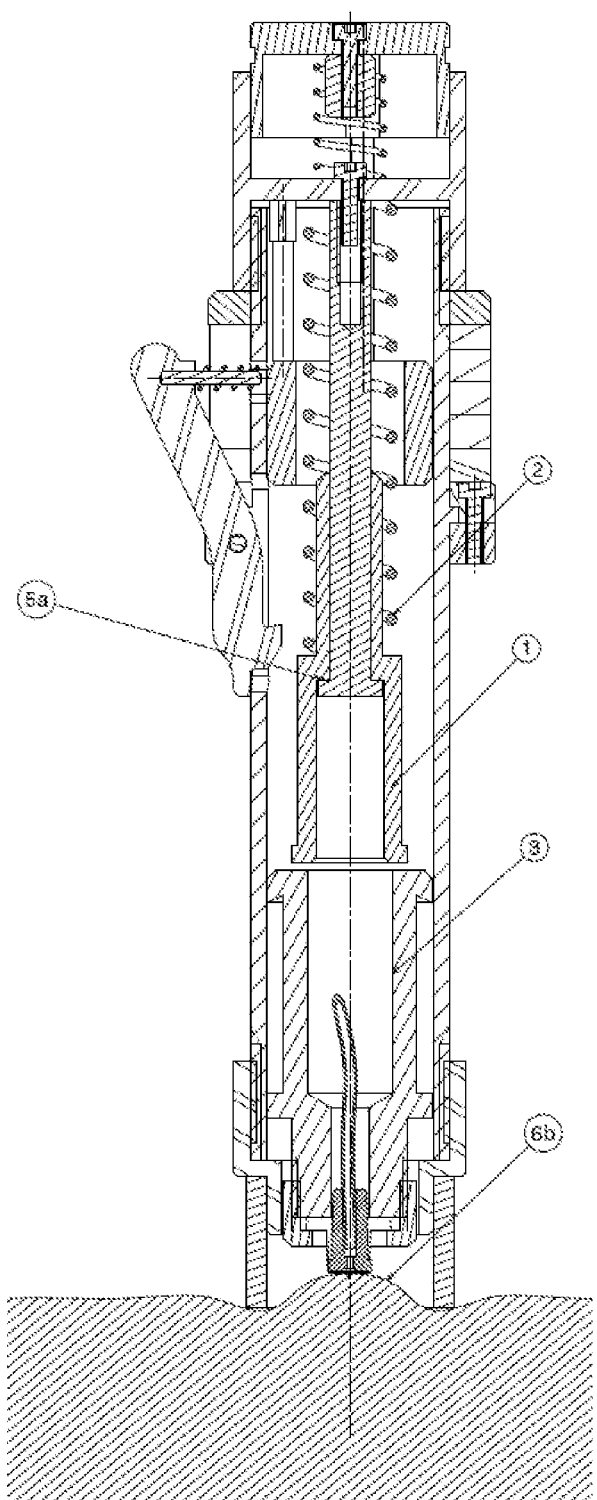

FIG. 9: In this variant, the opposing force of the thruster (1) is not applied, the height adopted by the piston (3) as a result of the formation of the papule (6b) being smaller than the free distance between the thruster (1) against the stop (5a) and the piston (3).

Figure 10:
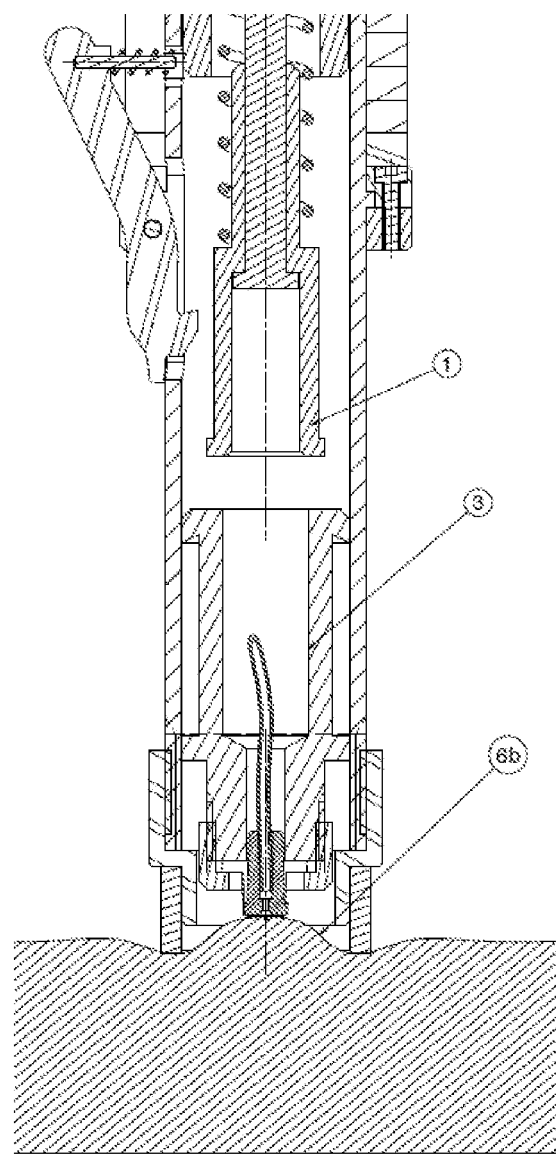

FIG. 10: In this other variant, at equilibrium, the thruster (1) is moved away (e.g. recompressed, spring relaxed upward, thruster stage raised) to leave the piston (3) empty space into which to rise as the papule (6b) forms. This is a return to the configuration of the initiator for injection, but ensuring the opposing force to the elastic force at the time of insertion.

Figure 11:
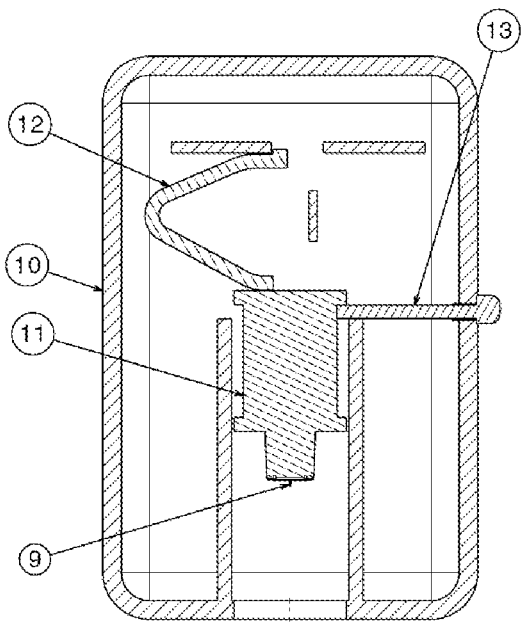

FIG. 11: Depiction of an embodiment of the device according to the invention. A needle (9) is secured to a piston (11). A leaf spring (12) is placed under spring-load between the piston (11) and the housing (10a).

Figure 12:
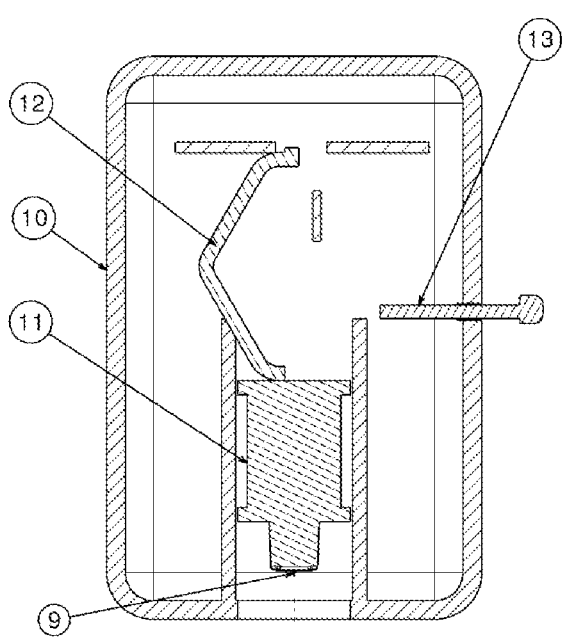
Figure 13:
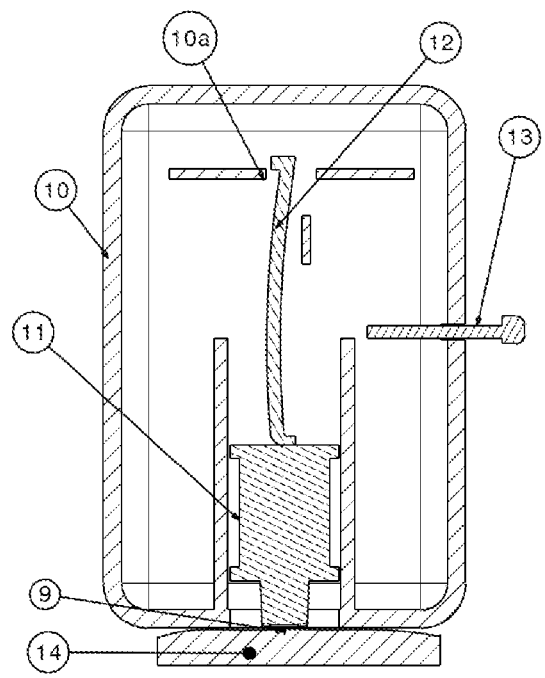

FIGS. 12-13: In this configuration, the device is placed on the tissue. The device has been triggered. The spring (12) relaxes and pushes the piston (11) which comes into abutment with the tissue (14). The piston (11) will continue its travel under the effect of inertia. In this configuration, the moment at which the leaf spring breaks contact with the housing (10a) corresponds on average to the moment at which the needle (9) begins to penetrate the tissue (14).

Figure 14:
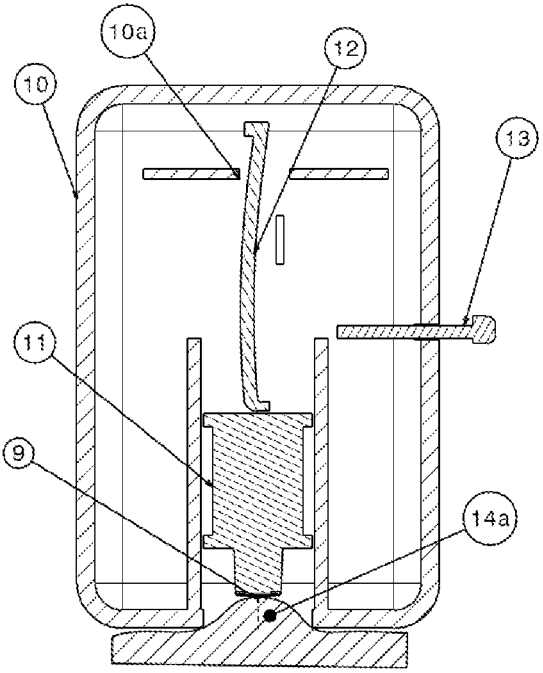

FIG. 14: The injection can begin, preferably at equilibrium, the papule (14a) that is forming pushes the piston (11) which can slide without putting up any great resistance to this sliding and allowing the needle (9) to remain correctly inserted in the papule (14a), guiding the movement. Here the spring (12) is decompressed and offers no opposing force that opposes the formation of the papule (14a).

Figure 15:
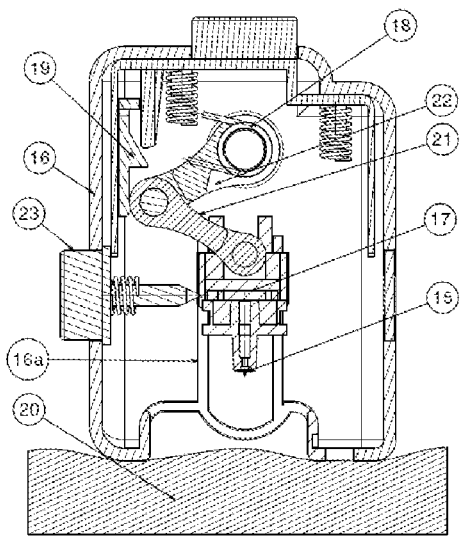

FIG. 15: Depiction of an embodiment of a device according to the invention. A needle (15) is secured to a piston (17). A mechanical "rod-crank" system (21, 22) allows the rotational movement brought about by the spring (18) to be converted into a translational movement of the piston (17). The piston (17) can slide in the guideways of the housing (16a).

Figure 16:
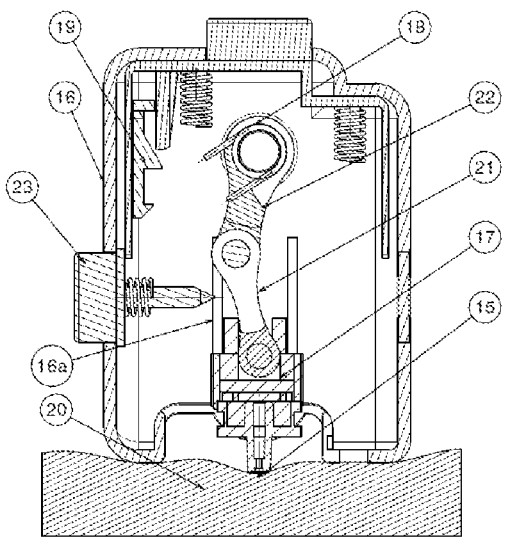

FIG. 16: In this configuration, the device is placed on the tissue. The device has been triggered. The spring (18) relaxes and activates the "rod-crank" system (21, 22) which pushes on the piston (17) that has just come into abutment against the tissue (16). The piston (11) will continue its travel under the effect of inertia.

For this configuration, the moment at which the spring is relaxed corresponds on average to the moment at which the needle (15) begins to penetrate the tissue (20).

For another configuration, the spring is able to maintain a certain force pressing the piston (17) against the tissue (20), pressing the button allows the force applied by the piton (17) to the tissue (20) to be released.

Figure 17:
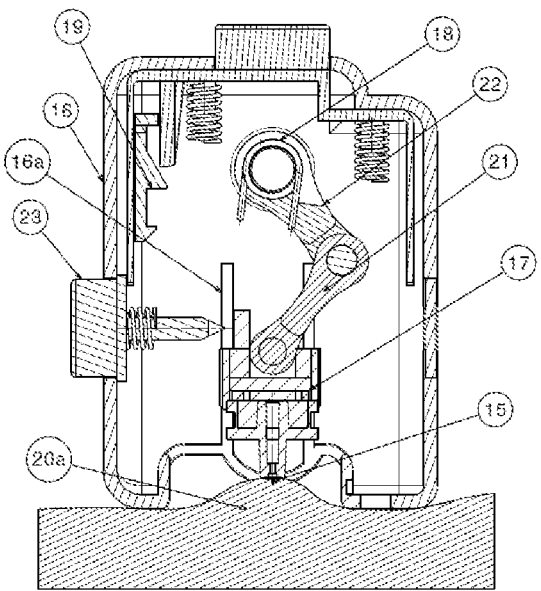

FIG. 17: Injection can begin, preferably at equilibrium, the papule (20a) that is forming pushes the piston (17) which can slide without offering a great deal of resistance and allowing the needle (15) to remain correctly inserted in the papule (20a), guiding the movement. Here, the spring (18) is decompressed and offers no opposing force opposing the formation of the papule (20a), the "rod-crank" system (21,22) allows the piston (17) to return as the papule (20a) forms.

The invention claimed is:

1. A method of intradermally injecting a solution into a patient tissue with a device for inserting needles, the device including a device body having a proximal end and a distal end which define a main axis, and a piston and a needle secured to the piston, the piston and the needle movable relative to the device body along a direction of the main axis, the needle projecting from a base, the base having a distal face, the method comprising the steps of:
   inserting the needle into the patient tissue;
   contacting a surface of the patient tissue with the distal face of the base; and
   injecting the solution into the patient tissue via the needle to deform the patient tissue and to form a papule in the patient tissue such that the papule makes the surface of the patient tissue urge against the piston to move the piston and the needle backwards relatively to the device body.

2. The method as claimed in claim 1, wherein the backwards moving of the piston is configured to reduce a force applied to the patient tissue.

3. The method as claimed in claim 1, further comprising the step of:
   placing the body of the device perpendicularly to the patient tissue.

4. The method as claimed in claim 1, further comprising the step of:
   maintaining the body of the device perpendicular to the patient tissue during the step of injecting.

5. The method as claimed in claim 1, further comprising the step of:
   orienting the device body of the device to penetrate the needle into the patient tissue at a specific angle.

6. The method as claimed in claim 5, wherein the specific angle is substantially perpendicular to the patient tissue.

7. The method as claimed in claim 1, wherein during the step of injecting, an opposing force of the piston relative to the device body is applied by a spring such that the needle remains inserted in the patient tissue.

8. The method as claimed in claim 1, further comprising the step of:
   contacting the surface of the patient tissue with the distal end of the device body.

* * * * *